US006695975B1

(12) United States Patent
Kneebone et al.

(10) Patent No.: US 6,695,975 B1
(45) Date of Patent: Feb. 24, 2004

(54) LIQUID FORMULATION

(75) Inventors: Graham Kneebone, Cambridge (GB); Smita Patel, Cambridge (GB)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 09/744,826

(22) PCT Filed: Jul. 19, 1999

(86) PCT No.: PCT/GB99/02162

§ 371 (c)(1), (2), (4) Date: Mar. 12, 2001

(87) PCT Pub. No.: WO00/07444

PCT Pub. Date: Feb. 17, 2000

(30) Foreign Application Priority Data

Jul. 31, 1998 (GB) ................................. 9916697

(51) Int. Cl.$^7$ .......................... C09K 3/00; A01N 25/30
(52) U.S. Cl. .......................... 252/182.11; 252/182.34; 504/116.1; 504/118; 504/139
(58) Field of Search .................... 252/182.11, 182.34; 504/116.1, 118, 139

(56) References Cited

U.S. PATENT DOCUMENTS

| 4,904,695 | A | * | 2/1990 | Bell ........................... 514/521 |
| 5,045,311 | A | * | 9/1991 | Pinter et al. .................. 514/75 |
| 5,192,793 | A | * | 3/1993 | Szekely et al. ............. 514/421 |
| 5,334,585 | A | | 8/1994 | Derian et al. |
| 5,362,707 | A | * | 11/1994 | Fiard et al. .................. 504/234 |
| 5,518,991 | A | * | 5/1996 | Frisch et al. ................ 504/138 |
| 5,700,472 | A | * | 12/1997 | Frisch et al. ................ 424/405 |
| 6,197,837 | B1 | * | 3/2001 | Hill et al. ...................... 516/41 |
| 6,245,216 | B1 | * | 6/2001 | Hill et al. ...................... 208/13 |
| 6,375,969 | B1 | * | 4/2002 | Kostka et al. ............... 424/409 |
| 6,391,952 | B1 | * | 5/2002 | Bett et al. .................... 524/160 |
| 6,416,775 | B1 | * | 7/2002 | Kostka et al. ............... 424/421 |
| 6,455,471 | B1 | | 9/2002 | Gubelmann-Bonneau et al. .......................... 504/133 |

FOREIGN PATENT DOCUMENTS

| EP | 160182 | * | 6/1985 |
| EP | 0257286 | | 3/1988 |
| EP | 0261492 | | 3/1988 |
| EP | 0297207 | | 1/1989 |
| EP | 0514769 | | 11/1992 |
| EP | 0789999 | | 8/1997 |
| HU | 9203487 | | 11/1992 |
| HU | 9503427 | | 2/1995 |
| HU | 214352 | | 1/1998 |
| HU | 214689 | | 3/1998 |
| WO | 9940784 | | 8/1999 |

* cited by examiner

*Primary Examiner*—Margaret Medley
(74) *Attorney, Agent, or Firm*—Ostrolenk, Faber, Gerb & Soffen, LLP

(57) ABSTRACT

The invention provides a suspo-emulsion formulation comprising defined first and second compatible components, the first component acting primarily as an oil emulsifier and secondarily as a particle dispersant, and the second component acting primarily as a particle dispersant and secondarily as an oil emulsifier. The invention enables the preparation of stable suspo-emulsions containing a variety of active ingredients and components and containing large quantities of oily components.

15 Claims, No Drawings

LIQUID FORMULATION

This invention relates to liquid formulations and methods for their preparation. In particular, the invention relates to liquid formulations that contain an emulsions phase and a suspended solid phase. Specifically, although not exclusively, the invention concerns formulations for use in agriculture, such as those containing pesticides, e.g. herbicides, fungicides and/or insecticides, where the formulations are diluted with water by an agricultural operator prior to application to the pest or its locus.

Creating stable emulsions that contain at least one solid component, so-called suspo-emulsions, presents significant challenges to the formulation chemist. These challenges increase the greater the number and complexity of the components. Suspo-emulsion formulations are especially sensitive to the shear forces during manufacture of the formulation, and also during dilution and mixing of the formulation with water by the agricultural operator. These forces accelerate hetero-flocculation, caused by agglomeration of the solid particles with droplets of the emulsion phase. Hetero-flocculation causes poor storage stability and may result in blocked nozzle filters during spraying of the diluted formulation by the agricultural operator. These problems are exacerbated when formulations contain large amounts of oily components which are often required to improve translocation of the active ingredient into the plant.

The challenge for the formulation chemist is to choose the right dispersants and emulsifiers to produce a stable system. Typically this is achieved by coating the solid particles with a polymer dispersant forming a steric layer around each particle; the oil component is then emulsified into the mixture with the aid of an emulsifier. The emulsion can be thermodynamically or kinetically stabilised. Kinetically stabilised systems will eventually coalesce back to a single oil phase, typically this takes about 2 to 3 years, i.e. the duration of the shelf life of the product. The thermodynamically stable systems spontaneously form microemulsion/solubilised systems when mixed together in the correct proportions.

Thus, attempts at providing stable suspo-emulsion formulations have typically involved the use of polymer dispersants to keep the droplets and particles physically apart. However these attempts have not found general applicability, because although they can be applied to specific, simple systems, they are not applicable to more complex suspo-emulsions. It is therefore the objective of the invention to provide a suspo-emulsion formulation that overcomes the above-mentioned problems.

According to the invention there is provided a suspo-emulsion formulation comprising first and second compatible components, the first component acting primarily as an oil emulsifier and secondarily as a particle dispersant, and the second component acting primarily as a particle dispersant and secondarily as an oil emulsifier, characterised in that, i) the first component consists of one or more compounds of formula $R^1(Y)_aH$;

ii) the second component consists of one or more compounds of formula

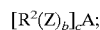

$[R^2(Z)_b]_cA$;

wherein $R^1$ and $R^2$, which may be the same or different, are substituted phenoxy;

Y and Z, which may be the same or different, are —$CHR^3CHR^4$—O—, where $R^3$ and $R^4$, which may be the same or different, are hydrogen or methyl;

a is 7 to 40;

b is 7 to 40;

c is 1 or 2; and

A is phosphate or sulfate radical (preferably phosphate), or salts thereof, wherein the concentration of the first component is greater than 70 g/liter.

The term suspo-emulsion, as known in the art, describes formulations wherein the continuous phase is water containing an emulsion and suspended particles. Emulsions can be "water-in-oil" emulsions where the oil phase is the major component surrounding aqueous particles or "oil-in-water" emulsions, where the aqueous phase is the major component. Our invention finds applicability in both systems, however it is particularly advantageous for use in water-in-oil suspo-emulsions.

Throughout this specification, unless the context requires otherwise, the word "comprise", or variations such as "comprises" or "comprising", will be understood to imply the inclusion of a stated integer or group of integers, but not the exclusion of any other integer or group of integers, including method steps.

Our invention enables the preparation of stable suspo-emulsions containing a variety of active ingredients and other components. It therefore finds more general applicability than prior art formulations. Moreover our invention enables the preparation of formulations containing much larger quantities of oily components than have hitherto been possible. We have found that formulations prepared in accordance with our invention are able to withstand high-shear conditions commonly experienced during manufacture and application of pesticides on to crops. Comparable systems, not utilising our invention, result in hetero-flocculation. By designing a system as described above where the dispersant and emulsifier are related, our invention goes against conventional teaching in the art and provides the formulation chemist with a new technical teaching which will find general applicability.

We have found that good performance is achieved when the amount of second component is between 15 to 50 g/liter, especially 25 and 35 g/liter.

We have found that our invention works particularly well when the formulation contains an ionic emulsifier. Salts of alkyl benzene sufonates are preferred, especially, calcium dodecyl benzene sulfonate.

Surprisingly we have found that suspo-emulsions when prepared in accordance with the invention form emulsions wherein the water/oil interface cannot easily be distinguished. These so-called microemulsions are characteristic of our invention particularly when the total concentration of the first component and the ionic emulsifier exceeds 150 g/liter.

We have found that enhanced performance is achieved when $R^1$ and/or $R^2$ are substituted by two or three 1-phenylethyl groups.

Furthermore, we have found that a and b, which may be the same or different, are preferably from 10 to 25, especially from 16 to 20.

The invention also includes formulations wherein the second component is a salt, preferably a sodium, potassium or triethanolamine salt Especially preferred is the triethanolamine salt.

It is particularly preferred that the first component comprises a compound of formula $R^1(Y)_aH$, where $R^1$ is tri-substituted phenoxy, substituted by a 1-phenylethyl radical at the 2, 4 and 6 positions, Y is —$CH_2CH_2$—O— and a is nominally 16. In the art this compound is known as ethoxylated tristyrylphenol (16 mole E.O.). Typically, this compound exists as a mixture with similar compounds.

It is particularly preferred that the second component comprises the triethanolamine salt of a compound of formula $[R^2(Z)_b]_c A$, where $R^2$ is tri-substituted phenoxy, substituted by a 1-phenylethyl radical at the 2,4 and 6 positions, Z is —$CH_2CH_2$—O—, b is nominally 20, c is 1 and A is phosphate. In the art this compound is known as a ethoxylated tristyrylphenol phosphate (20 mole E.O.). Typically, this compound exists as a mixture with similar compounds, particularly with similar compounds where c is 2.

Our invention finds application particularly in the technical field of pesticide formulation, where many active ingredients exhibit low solubility in both aqueous and organic solvents. Such active ingredients include fluquinconazole, carbendazim and isoproturon.

Our invention finds particular applicability in the preparation of formulations comprising two or more active ingredients, especially where one ingredient is a high melting point, water insoluble solid and another ingredient is dissolved in a non water-miscible liquid such as rape oil or mineral oil, e.g. prochloraz.

EXAMPLES

The invention will now be shown, by way of example only, with reference to the following Examples.

Example 1

Choice of Non-ionic Emulsifier and Dispersant on Formulation Stability

Formulations 1, 2 and 3 were prepared according to the following method.

Preparation

Ingredients 1 to 5 were mixed in the proportions shown in Table 1 to form a solution. Ingredients 6 to 12 were mixed in the proportions shown in Table 1 and ground in a bead-mill until the fluqinconazole had a median diameter of 2 microns. Both sets of ingredients were then mixed to produce the resulting formulation. As can be seen in Table 1, the ingredients of each formulation remained constant except for ingredients 4 and 10.

Compound I is of formula $R^1(Y)_a H$, where $R^1$ is tri-substituted phenoxy, substituted by a 1-phenylethyl radical at the 2,4 and 6 positions, Y is —$CH_2CH_2$—O— and a is nominally 16. In the art this compound is known as a ethoxylated tristyrylphenol (16 mole E.O.). Typically, this compound exists as a mixture with similar compounds.

Compound of formula II is the triethanolamine salt of a compound of formula $[R^2(Z)_b]_c A$, where $R^2$ is tri-substituted phenoxy, substituted by a 1-phenylethyl radical at the 2,4 and 6 positions, Z is —$CH_2CH_2$—O—, b is nominally 20, c is 1 and A is phosphate. In the art this compound is known as a ethoxylated tristyrylphenol phosphate (20 mole E.O.). Typically, this compound exists as a mixture with similar compounds, particularly with similar compounds where c is 2.

Test Method

The stability of the formulations was tested using a laboratory scale spray rig that was designed to simulate field conditions. Each diluted formulation was re-circulated vigorously for at least half an hour using a high power circulation pump to simulate the shear forces that would be experienced in the spray tank in practice. A pre-weighed filter is positioned in an arm at right angles to the re-circulation flow and the flow through the filter is regulated so as to encourage deposition of any residue.

Stability of the formulations was assessed in a number of ways. A formulation was classified as having failed if after re-circulation at least one of the following applied:

i) the weight of residue on the filter was greater than 0.02% of the original weight of formulation used, ii) there was a large build-up on the walls and floor of the beaker, iii) there was a sticky tide mark on the walls of the beaker, iv) microscopic evaluation revealed hetero-flocculation had occurred.

All four criteria were considered in determining how a formulation had performed. The test results are shown in Table 1.

TABLE 1

| Ingredient | mass/g | Formulation 1 | Formulation 2 | Formulation 3 |
|---|---|---|---|---|
| 1 Prochloraz | 174 | — | — | — |
| 2 Penetrant | 174 | — | — | — |
| 3 Aromatic solvent | 190 | — | — | — |
| 4 Non-ionic Emulsifier | 215 | Compound I | Compound I | Castor oil ethoxylate (40 mole EO) |
| 5 Ionic Emulsifier | 92 | — | — | — |
| 6 Fluquinconazole | 54 | — | — | — |
| 7 Antifreeze | 66 | — | — | — |
| 8 Antifoam | 2 | — | — | — |
| 9 Crystallisation inhibitor | 38 | — | — | — |
| 10 Dispersant | 30 | Compound II | Oleyl methyl tauride | Compound II |
| 11 Biocide | 2 | — | — | — |
| 12 Water | make up to 1 liter | — | — | — |
| TEST RESULTS | | PASS | FAIL | FAIL |

The results show that formulations made in accordance with the invention are resistant to hetero-flocculation.

Example 2

Effect of Concentration of Compound I (Non-ionic Emulsifier) and Compound II (Dispersant) on Formulation Stability Formulations 4 to 10 were prepared according to the preparative method described in Example 1 in proportions shown in Table 2 The proportions are shown in grams. Table 2 also shows the test results which were assessed using the same criteria as in Example 1.

TABLE 2

| Ingredient | 4 | 5 | 6 | 7 | 8 | 9 | 10 |
|---|---|---|---|---|---|---|---|
| 1 Prochloraz | 174 | 174 | 174 | 174 | 174 | 174 | 174 |
| 2 Penetrant | 174 | 174 | 174 | 174 | 174 | 174 | 174 |
| 3 Aromatic solvent | 190 | 190 | 190 | 190 | 190 | 190 | 190 |
| 4 Compound I | 70 | 105 | 122.5 | 126 | 140 | 175 | 215 |
| 5 Ionic Emulsifier | 30 | 45 | 52.5 | 54 | 60 | 75 | 92 |
| 6 Fluquinconazole | 54 | 54 | 54 | 54 | 54 | 54 | 54 |
| 7 Antifreeze | 66 | 66 | 66 | 66 | 66 | 66 | 66 |
| 8 Antifoam | 2 | 2 | 2 | 2 | 2 | 2 | 2 |
| 9 Crystallisation inhibitor | 38 | 38 | 38 | 38 | 38 | 38 | 38 |
| 10 Compound II | 25 | 25 | 25 | 25 | 25 | 25 | 25 |
| 11 Biocide | 2 | 2 | 2 | 2 | 2 | 2 | 2 |

TABLE 2-continued

| Ingredient | 4 | 5 | 6 | 7 | 8 | 9 | 10 |
|---|---|---|---|---|---|---|---|
| 12 Water (make up to 1 liter) | | | | | | | |
| TEST RESULTS | FAIL | PASS | PASS | PASS | PASS | PASS | PASS |

The results show that hetero-flocculation occurs when the amount of compound I falls below 70 g/liter.

What is claimed is:

1. A suspo-emulsion formulation comprising first and second compatible components, the first component acting primarily as an oil emulsifier and secondarily as a particle dispersant, and the second component acting primarily as a particle dispersant and secondarily as an oil emulsifier, characterized in that,
    i) the first component consists of one or more compounds of formula $R^1(Y)_aH$;
    ii) the second component consists of one or more compounds of formula $[R^2(Z)_b]_cA$; wherein
        $R^1$ and $R^2$, which may be the same or different, are substituted phenoxy;
        Y and Z, which may be the same or different, are —$CHR^3CHR^4$—O—, where $R^3$ and $R^4$, which may be the same or different, are hydrogen or methyl;
        a is 7 to 40;
        b is 7 to 40;
        c is 1 or 2; and
        A is phosphate or sulfate radical, or salts thereof,
            wherein the concentration of the first component is greater than 70 grams per liter of emulsion, and wherein the amount of second component is between 15 to 50 grams per liter of emulsion isoproturon.

2. A formulation according to claim 1 which further contains an ionic emulsifier.

3. A formulation according to claim 1 wherein the amount of second component is between 25 and 35 grams per liter of emulsion.

4. A formulation according to claim 2 which is a microemulsion wherein the total concentration of the first component and the ionic emulsifier exceeds 150 grams per liter of emulsion.

5. A formulation according to claim 2 wherein the ionic emulsifier is a salt of an alkyl benzene sulfonate.

6. A formulation according to claim 4 wherein the first component is ethoxylated tristyrylphenol (16 mole E.O.) and the second component is an ethoxylated tristyrylphenol phosphate (20 mole E.O.).

7. A formulation according to claim 1 wherein at least one of $R^1$ and $R^2$ are substituted by two or three 1-phenylethyl groups.

8. A formulation according to claim 1 wherein a and b, which may be the same or different, are from 10 to 25.

9. A formulation according to claim 1 wherein a and b, which may be the same or different, are from 16 to 20.

10. A formulation according to claim 1 wherein A is phosphate.

11. A formulation according to claim 1 wherein the second component is a sodium, potassium or triethanolamine salt.

12. A formulation according to claim 1 wherein the first component comprises a compound of formula $R^1(Y)_aH$, where R1 is tri-substituted phenoxy, substituted by a 1-phenylethyl radical at the 2, 4 and 6 positions, Y is —$CH_2CH_2$—O— and a is nominally 16.

13. A formulation according to claim 1 wherein the second component comprises the triethanolamine salt of a compound of formula $[R^2(Z)_b]_cA$, where $R^2$ is tri-substituted phenoxy, substituted by a 1-phenylethyl radical at the 2, 4 and 6 positions, Z is —$CH_2CH_2$—O—, b is nominally 20, c is 1 and A is phosphate.

14. A formulation according to claim 1 which further contains at least one active ingredient exhibiting low solubility in both aqueous and organic solvents.

15. A formulation according to claim 6 further containing at least one active ingredient selected from the group consisting of prochloraz, fluquinconazole, carbendazim and isoproturon.

\* \* \* \* \*